US006174519B1

(12) United States Patent
Greene

(10) Patent No.: US 6,174,519 B1
(45) Date of Patent: Jan. 16, 2001

(54) COMPOSITION FOR PROTECTING SKIN FROM DAMAGING EFFECTS OF ULTRAVIOLET LIGHT

(75) Inventor: James A. Greene, Sunnyvale, CA (US)

(73) Assignee: Shaklee Corporation, Pleasanton, CA (US)

( * ) Notice: Under 35 U.S.C. 154(b), the term of this patent shall be extended for 0 days.

(21) Appl. No.: 09/441,396

(22) Filed: Nov. 16, 1999

Related U.S. Application Data

(63) Continuation of application No. 08/998,238, filed on Dec. 24, 1997.

(51) Int. Cl.$^7$ ..................................................... A61K 7/42
(52) U.S. Cl. ........................... 424/59; 424/60; 424/195.1; 424/401; 424/451; 514/561; 514/567; 514/772.3; 514/772.4; 514/844; 514/846; 514/847; 514/937; 514/938
(58) Field of Search ........................... 424/59, 60, 195.1, 424/401, 451; 514/561, 567, 772.3, 772.4, 844, 846, 847, 937, 938

(56) References Cited

U.S. PATENT DOCUMENTS

| | | |
|---|---|---|
| Re. 33,845 | 3/1992 | Schreuder . |
| 2,400,171 | 5/1946 | Ruskin . |
| 2,442,461 | 6/1948 | Karrer . |
| 2,585,580 | 2/1952 | Oppit . |
| 4,209,449 | 6/1980 | Mayhew et al. . |
| 4,367,157 | 1/1983 | Sherman . |
| 4,372,874 | 2/1983 | Modrovich . |
| 4,380,503 | 4/1983 | Koerner et al. . |
| 4,454,112 | 6/1984 | Tuominen . |
| 4,503,002 | 3/1985 | Mayhew et al. . |
| 4,563,346 | 1/1986 | Deckner . |
| 4,603,046 | 7/1986 | Georgalas et al. . |
| 4,698,178 | 10/1987 | Hüttinger et al. . |
| 4,784,845 | 11/1988 | Desai et al. . |
| 4,826,691 | 5/1989 | Prochnow . |
| 4,833,259 | 5/1989 | Erlemann et al. . |
| 4,847,267 | 7/1989 | Deckner et al. . |
| 4,904,698 | 2/1990 | Adkins, Jr. et al. . |
| 4,938,960 | 7/1990 | Ismail . |
| 4,940,574 | 7/1990 | Kaplan . |
| 5,008,100 | 4/1991 | Zecchino et al. . |
| 5,140,043 | 8/1992 | Darr et al. . |
| 5,141,665 | 8/1992 | Sherman . |
| 5,153,230 | 10/1992 | Jaffery . |
| 5,162,378 | 11/1992 | Guthauser . |
| 5,215,976 | 6/1993 | Fost et al. . |
| 5,286,719 | 2/1994 | Fost et al. . |
| 5,290,481 | 3/1994 | Todd, Jr. . |
| 5,290,555 | 3/1994 | Guthauser et al. . |
| 5,296,249 | 3/1994 | Todd, Jr. . |
| 5,308,621 | 5/1994 | Taylor et al. . |
| 5,372,805 | 12/1994 | Finkel et al. . |
| 5,374,362 | 12/1994 | McFarland . |
| 5,378,461 | 1/1995 | Neigut . |
| 5,384,115 | 1/1995 | Bissett et al. . |
| 5,391,321 | 2/1995 | Grüning et al. . |
| 5,445,823 | 8/1995 | Hall et al. . |
| 5,447,715 | 9/1995 | Roberts . |
| 5,482,705 | 1/1996 | Hoffmann, Jr. et al. . |
| 5,482,714 | 1/1996 | Jones et al. . |
| 5,505,935 * | 4/1996 | Guerrero et al. ....................... 424/59 |
| 5,516,506 | 5/1996 | Fogel . |
| 5,543,135 | 8/1996 | Dahms . |
| 5,543,136 | 8/1996 | Aldous . |
| 5,560,917 | 10/1996 | Cohen et al. . |
| 5,573,754 | 11/1996 | Kulkarni et al. . |
| 5,573,785 | 11/1996 | Murphy . |
| 5,587,149 | 12/1996 | Punto et al. . |
| 5,587,151 | 12/1996 | Richard et al. . |
| 5,599,533 | 2/1997 | Stepniewski et al. . |
| 5,601,806 | 2/1997 | Katsumata et al. . |
| 5,605,694 | 2/1997 | Nadaud et al. . |
| 5,607,921 | 3/1997 | Bernard et al. . |
| 5,663,205 | 9/1997 | Ogawa et al. . |
| 5,663,270 | 9/1997 | Richard et al. . |
| 5,670,160 | 9/1997 | Eggensperger . |
| 5,738,859 | 4/1998 | Posner . |
| 5,746,945 | 5/1998 | Ryklin et al. . |
| 5,759,523 | 6/1998 | Hughes et al. . |
| 5,804,168 | 9/1998 | Murad . |
| 5,916,573 * | 6/1999 | Spiers et al. ....................... 424/195.1 |
| 6,015,548 * | 1/2000 | Siddiqui et al. ....................... 424/59 |

FOREIGN PATENT DOCUMENTS

| | | |
|---|---|---|
| 0551030 | 9/1993 | (SU) . |
| WO 96/00060 | 1/1996 | (WO) . |

OTHER PUBLICATIONS

Rigler, N.E. and Schimmel, J., "Preservation of Cosmetics," in Cosmetics: Science and Technology, Chapter 43:1034–1074 (Ed: Sagarin) Interscience Publishers, Inc., New York (1957).

DeRitter et al., Effect of Silica Gel on Stability and Biological Availability of Ascorbic Acid, *Journal of Pharmaceutical Sciences* 59:229–233 (1970).

(List continued on next page.)

Primary Examiner—James O. Wilson
(74) Attorney, Agent, or Firm—Klarquist Sparkman Campbell Leigh & Whinston, LLP

(57) ABSTRACT

A topical antioxidant composition for the protection of skin from damage caused by ultraviolet radiation. The composition includes a first component (such as beta glucan) that increases cellular viability of epidermal cells, and a second component that decreases the production of inflammatory mediators, such as prostaglandins in those cells. In a particular embodiment, the composition includes beta glucan in combination with panthenol, grape seed extract, vitamin C and superoxide dismutase, which exhibit a synergistic effect in protecting the skin from the adverse effects of ultraviolet radiation. In another embodiment, the composition further includes Vitamin A and Vitamin E. The antioxidant compositions are incorporated into sunscreen products, soap, moisturizing lotions, skin toners, and other skin care products.

20 Claims, No Drawings

OTHER PUBLICATIONS

Harry, R.G., "Preservatives and Antioxidants," in *Harry's Cosmeticology: The Principles and Practice of Modern Cosmetics*, Chapter 41:655–690 (Ed: Harry) Leonard Hill Books, London (1973).

Manowitz, M. and Sharpell, F., "Preservation of Cosmetics," in *Disinfection, Sterilization, and Preservation*, Chapter 39:768–787 (Ed: Block) Lea & Febiger, Philadelphia (1977).

Larrosa et al., Antiproliferative Effect of Intravitreal α–Tocopherol and α–Tocopherol–Acid–Succinate in a Rabbit Model of PVR, *Current Eye Research* 1030–1035 (1987).

Darr et al., Topical Vitamin C Protects Porcine Skin From Ultraviolet Radiation–Induced Damage, *British Journal of Dermatology* 127:247–253 (1992).

Idson, B., Vitamins and the Skin, *Cosmetics & Toiletries* 108:79–94 (1993).

Mayer et al., The Effects of Vitamin E on the Skin, *Cosmetics & Toiletries* 108:99–109 (1993).

Rieger, M.M., Oxidative Reactions in and on Skin: Mechanism and Prevention, *Cosmetics & Toiletries* 108:43–56 (1993).

Paton et al., Oats: Chemistry, Technology and Potential Uses in the Cosmetic Industry, *Cosmetics & Toiletries* 110:63–70 (1995).

Palmieri et al., Vitamin E Added Silicon Gel Sheets for Treatment of Hypertrophic Scars and Keloids, *International Journal of Dermatology* 34:506–509 (1995).

Alberts et al., Disposition and Metabolism of Topically Adminstered α–Tocopherol Acetate: A Common Ingredient of Commercially Available Sunscreens and Cosmetics, *Nutrition and Cancer* 26:193–201 (1996).

Gensler et al., Importance of the Form of Topical Vitamin E for the Prevention of Photocarcinogenesis, *Nutrition and Cancer* 26:183–191 (1996).

VERIS Research Summary, The Role of Antioxidants in Skin Care and Protection, *VERIS Research Infomation Service*, May 1997.

* cited by examiner

COMPOSITION FOR PROTECTING SKIN FROM DAMAGING EFFECTS OF ULTRAVIOLET LIGHT

This application is a continuation of Ser. No. 08/998,238 filed Dec. 24, 1997.

FIELD OF THE INVENTION

This invention concerns a topical antioxidant composition for the protection and treatment of human skin, particularly skin that is exposed to harmful ultraviolet radiation.

BACKGROUND OF THE INVENTION

The ultraviolet (UV) wavelengths of sunlight can cause sunburn (erythema) and blistering (edema). Exposure to ultraviolet light can also cause the skin to feel dry and taut in moderate doses, and to peel if exposed to higher doses. These acute, or short term, effects are readily perceptible. However, there are also more subtle acute effects that are not as readily discernable, such as photo-immunosuppression, cross-linking of deoxyribonucleic acid (DNA), formation of sunburn cells, and loss of Langerhans cells. Even more serious long term effects can occur, such as skin cancer and premature aging of the skin.

Human skin can be protected from some of these environmental effects. Moisturizers can readily reverse the appearance of dryness regardless of whether it results from low humidity conditions or UV light, and relieve the tautness of the skin caused by UV light exposure. These products either attract moisture from the environment to the skin's surface, or reduce the amount of moisture in the skin that can escape into the environment. These products also add needed moisture to the skin from the formulation itself, and add a layer of emollients on the skin surface to leave it softer and more supple.

Sunscreen products are known to protect the skin from some of the harmful effects of ultraviolet light exposure. These products contain molecules that absorb the harmful wavelengths of ultraviolet light before they can reach the skin. The absorbed light is converted to heat and rapidly dissipated to the skin and environment, which allows these molecules to revert to a lower energy state, and subsequently absorb another photon of light. In this manner, sunscreen agents can absorb numerous photons of ultraviolet light in a relatively short period of time. By absorbing the harmful wavelengths of light, sunscreen products prevent many of the acute and chronic effects caused by ultraviolet light.

However, sunscreen products are not perfect in their mode of action. There is no single sunscreen agent that is capable of absorbing all of the harmful wavelengths striking the skin. Higher Sun Protection Factor (SPF) formulations address this problem by including a combination of sunscreen agents in the formulation. However, even when using a combination of sunscreen agents, these products do not provide complete protection, particularly from the longer ultraviolet wavelengths. Although these longer wavelengths do not readily elicit many of the acute damaging effects commonly attributed to ultraviolet light exposure, recent research indicates that these wavelengths can create free radicals in the skin. These free radicals may be responsible for the premature aging of the skin commonly linked to ultraviolet light exposure.

According to the free radical theory of premature aging of the skin, ultraviolet light can produce reactive oxygen species (ROS) that damage the skin. ROS are a collection of reactive free radicals produced from the oxygen molecule, and include singlet oxygen, the superoxide radical, hydrogen peroxide, and the hydroxyl radical, as well as the reaction products produced by these free radicals. Due to their reactivity, ROS relatively indiscriminately react with other molecules, and generate a cascade of harmful free radical reactions in the skin.

The skin possesses defense mechanisms against the generation of ROS. These defenses include the presence of enzymes such as superoxide dismutase, catalase, glutathione transferase, glutathione peroxidase and glutathione reductase, as well as antioxidants such as tocopherols, ubiquinone, ubiquinol, ascorbic acid and dehydroascorbic acid. Unfortunately, ultraviolet light entering the skin can easily overwhelm these defense systems, such that the amount of superoxide dismutase and glutathione transferase in the skin declines significantly upon irradiation with solar simulated ultraviolet light. Simultaneous with the loss of these reducing enzymes, there is a dramatic increase in conjugated double bonds formed in the skin from the linoleates present in cell membranes. There is also an increase in thiobarbituric acid reactive substances present in the skin, which represent a collection of molecules that are formed from ROS.

Prostaglandins are a mediator of inflammation that is believed to be produced by skin damage, and ROS may create conditions that promote the formation of prostaglandins and sunburn cells. These mediators of inflammation are formed from arachidonic acid upon oxidation via the lipoxygenase pathway. Although this oxidation is normally enzymatically controlled, the increase in prostaglandins in skin after ultraviolet irradiation may also be a result of the generation of ROS. Additionally, there are other messenger systems in skin cells that could increase the amount of prostaglandins that are activated by reactions involving ROS.

Sunburn cells are prematurely dead keratinocytes that are produced in skin as a result of ultraviolet light exposure. The contribution of ROS to the formation of sunburn cells has not been adequately researched. However, given the fact that ROS produce negative effects upon molecules in the cell membranes as well as in proteins including enzymes that control most cellular activity, it has been suggested that ROS could play a potentially important role in the formation of sunburn cells.

Since sunscreens are unable to completely protect the skin against the adverse effects of ultraviolet radiation, alternative modes of protection have been proposed. Vitamins, such as Vitamin E acetate, have been shown to make the skin softer and smoother after topical application, which can offset some of the damaging effects of the sun. Vitamin A palmitate has been shown to create smoother skin and help enhance the process of cellular turnover. This enhancement rids the skin of the outermost dead layer of skin by bringing more youthful appearing skin cells to the surface. Other materials, such as hyaluronic acid and pyrrolidone carboxylic acid (PCA), have also been used for their ability to enhance the moisture binding capacity of the skin and therefore lead to smoother, softer skin.

Compositions that incorporate Vitamins A or E, or their derivatives, in sunscreen compositions, are shown in U.S. Pat. Nos. 4,454,112; 5,532,805; and 5,378,461. The use of Vitamin C in combination with Vitamins A, E, B and other agents in a skin protectant composition, is described in U.S. Pat. No. 4,938,960. An antioxidant preparation that is said to protect the skin against harmful ultraviolet radiation is disclosed in U.S. Pat. No. 5,607,921, and contains Vitamin C, in combination with Vitamins A and E, and monosaccharide or amide precursors. Sunscreen compositions containing panthenol and other agents are disclosed in U.S. Pat. Nos. RE 33,845; 5,505,935; 5,445,823; and 5,573,754. The antioxidant effect of superoxide dismutase when externally applied to the skin to protect against the effects of ultraviolet radiation is also described in U.S. Pat. No. 5,601,806.

In spite of advances in recent years in the protection of skin from harmful ultraviolet radiation, the epidemic of skin cancer and skin damage from the effects of this radiation has continued unabated. The loss of portions of the ozone layer from environmental pollution is believed to have contributed to an increase in ambient ultraviolet radiation that reaches exposed skin. Many skin protection preparations that could prevent sun damage have an unacceptable odor or texture that discourages their more frequent use, and many of the available skin protectants do not sufficiently protect the skin from these many mechanisms of injury. Hence there is a significant public health need for commercially acceptable or improved preparations that can be topically applied to human and animal skin, to offset the harmful effects of ultraviolet radiation.

It is therefore an object of the invention to provide a therapeutic or cosmetic composition containing new antioxidants, or agents that reduce sun induced skin damage and inflammation by aborting the production of prostaglandins in the skin.

It is another object of the invention to provide such a composition having a superior therapeutic or cosmetic effect.

Yet another object is to provide such compositions that have characteristics that will encourage their use.

SUMMARY OF THE INVENTION

The foregoing objects are achieved by the present invention, which is a composition and method for inhibiting skin damage induced by ultraviolet radiation, by applying topically to the skin an antioxidant composition which includes beta glucan in a sufficient amount to protect the skin from damaging effects of ultraviolet radiation. Beta glucan has not previously been reported to act as a skin protectant against the harmful effects of ultraviolet radiation. In disclosed embodiments, the composition further includes panthenol, grape seed extract, Vitamin C, and superoxide dismutase, which act synergistically with the beta glucan to improve cellular viability and reduce the production of inflammatory prostaglandin $PGE_2$ in skin exposed to ultraviolet radiation. The composition can also include Vitamin A (retinol) and Vitamin E (tocopherol), which also act synergistically as an antioxidant in the skin.

In particular embodiments, the composition includes at least 0.005% beta glucan, 0.005% panthenol, 0.00001% grape seed extract, 0.0001% Vitamin C, and 0.0001% superoxide dismutase. For example, the composition may contain 0.005–5.00% beta glucan, 0.005–5.00% panthenol, 0.00001–1.00% grape seed extract, 0.0001–3.00% Vitamin C, and 0.0001–1.0000% superoxide dismutase. The composition may further include at least 0.0005% Vitamin A, and at least 0.05% Vitamin E, for example 0.0005–0.50% Vitamin A, and 0.05–30.00% Vitamin E. All percent compositions are given by weight in this specification.

In more specific embodiments, the topical composition includes beta glucan in a sufficient amount to improve cellular viability in the skin when applied topically before or after exposure to ultraviolet radiation, and at least one other skin protectant that reduces skin damage caused by ultraviolet light. The skin protectant may be selected from the group consisting of one or more of panthenol, grape seed extract, Vitamin C, superoxide dismutase, Vitamin A or Vitamin E in a sufficient amount to reduce production of $PGE_2$, or increase cellular viability, in the skin when applied topically. The Vitamin C may be in the form of magnesium ascorbyl phosphate, while the Vitamin A may be in the form of Vitamin A palmitate, and the Vitamin E may be in the form of Vitamin E acetate.

The composition of the present invention may be provided in an aqueous or non-aqueous solution, suspension or an emulsion (water-in-oil or oil-in-water). The composition may be a skin toner composition, a moisturizing lotion, a sunscreen composition, a skin cleanser, or any other skin treatment composition. The composition may also be used in methods of protecting skin against the harmful effects of ultraviolet radiation, by applying topically to the skin an amount of the composition effective to reduce the production of $PGE_2$ in the skin, or improve cellular viability. The composition may be applied before or after exposure to the sun, but is preferably applied prior to sun exposure, for example immediately before sun exposure.

The foregoing and other objects, features, and advantages of the invention will become more apparent from the following detailed description of a preferred embodiment.

DETAILED DESCRIPTION OF A PREFERRED EMBODIMENT

Given the known effects of ultraviolet radiation on the skin, the inadequacy of many present skin protectants to interfere with the mechanisms of cellular damage, and the reluctance of the public to regularly wear sufficient sunscreen protection to block the damaging effects of ultraviolet light, there is a need for effective alternative products that provide protection from the harmful effects of ultraviolet light. The present invention achieves these objectives by combining several antioxidants in a consumer acceptable form, which at the same time very effectively mitigates the damaging effects of sunlight on the skin. Additionally, the combination of antioxidants in the present composition provides unexpectedly superior protection against the damaging effects of ultraviolet light exposure to that provided by the individual antioxidants, as shown in the following Examples.

EXAMPLE 1

Cellular Viability Assay

Antioxidant activity for these mixtures of antioxidants was evaluated in cell culture using the Epiderm Skin Model (EPI-100) from the Mattek Corporation of Ashland, Mass. These cell cultures of neonatal foreskin were cultured in accordance with the manufacturer's directions, and were assayed for percent cellular viability by measuring the amount of 3-(4,5-dimethylthazol-2-yl)-2,5-diphenyltetrazolium bromide (MTT) dye taken up by the cell cultures. Viable cells take up this dye and convert it to insoluble formazin crystals that resides in the mitochondria of the cells until extracted with alcohol. The amount of MTT converted to extractable formazin crystals is directly proportional to the viability of the cell culture. MTT is measured spectrophotometrically. Cells exposed to UV light at a rate of 1.5 Minimal Erythemal Dose (MED) per hour per square centimeter from a solar simulator (filtered to yield wavelengths in the region of 290–400 nm) in the presence of the antioxidant ingredient or mixtures were used to measure the effect of antioxidants to protect the cell culture from the generation of free radicals. The total dose of ultraviolet light was 31.5 $mJ/cm^2$.

The controls for this portion of the study were cell cultures without added antioxidants (positive control). All cell cultures were also compared to cultures that were not exposed to UV light and did not include antioxidant agents or blends in order to determine percent cellular viability (negative control). This latter measurement was assumed to be equal to 100% viability. Three cell cultures were run for each antioxidant ingredient, blend or control sample tested. The results for these assays were then averaged.

EXAMPLE 2

PGE$_2$ Production Assay

The cell cultures were also evaluated for the production of Prostaglandin E$_2$ (PGE$_2$) using an assay kit obtained from PerSpective Diagnostics of Cambridge, Mass. As with the assay for percent cellular viability, the cell cultures were exposed to a dose of ultraviolet light at a rate of 1.5 MED per hour per square centimeter from a solar simulator in the presence of the antioxidant ingredients, blends or controls. The total dose of ultraviolet light was 31.5 mJ/cm$^2$. These cell cultures were then allowed to stand in normal growth media for 24 hours. After being allowed to grow for that period of time, the cell cultures were assayed for production of PGE$_2$ using the assay kit from PerSpective Diagnostics. The controls for this portion of the study were cell cultures exposed to the same dose of ultraviolet radiation but without added antioxidants (positive control). Three cell cultures were run for each antioxidant ingredient, blend or control sample tested. The results for these assays were then averaged. The results of these tests are shown in Tables 1 and 2.

The results shown in Table 1 indicate that all of the antioxidant agents and blends of these agents exhibit significant protective effect from ultraviolet light induced free radicals as measured by percent cellular viability. This activity must be as a result of the antioxidant effect because none of these agents exhibit any significant absorption in the solar ultraviolet wavelengths (290 to 400 nm) at the concentrations tested. Percent cellular viability after light exposure for blends A, B, and C is found in the data presented in Table 3. Although there are some statistically significant differences between individual antioxidant ingredients, the primary statistical differences are found between the blends of the agents and the individual agents composing the blends. For example, Blend B, composed of beta glucan, DL panthenol, grape seed extract, magnesium ascorbyl phosphate and superoxide dismutase, provides statistically superior protection to each of its individual components other than DL panthenol (data not shown). It might have been statistically superior to DL panthenol if the standard deviation of this antioxidant agent had been smaller. Blend A, composed of Vitamin E Acetate and Vitamin A palmitate, provides statistically superior protection when compared to its constituent ingredients at the 90% confidence level.

TABLE 1

Percent Cellular Viability Resulting from UV Light Exposure

| Antioxidant Agent Tested | Average Percent Viability + Standard Deviation | Statistically Different from UV Irradiation Only (Confidence Level)[1] |
|---|---|---|
| Beta Glucan | 43.6 ± 2.78 | Yes (95%) |
| DL Panthenol | 46.3 ± 14.9 | Yes (80%) |
| Grape Seed Extract | 39.6 ± 0.48 | Yes (95%) |
| Magnesium Ascorbyl Phosphate[2] | 45.1 ± 2.34 | Yes (95%) |
| Superoxide Dismutase | 43.0 ± 3.30 | Yes (90%) |
| Vitamin A Palmitate | 42.0 ± 4.98 | Yes (95%) |
| Vitamin E Acetate | 43.6 ± 2.62 | Yes (95%) |
| Blend A[3] | 58.7 ± 8.56 | Yes (95%) |
| Blend B[4] | 51.1 ± 3.87 | Yes (95%) |
| UV Irradiation Only[5] | 28.4 ± 5.15 | — |

[1]The level of statistical confidence is based upon hypothesis testing using a Student t test.
[2]This a stabilized form of Vitamin C (Ascorbic Acid).
[3]Blend A is composed of Vitamin A palmitate and Vitamin E acetate.
[4]Blend B is composed of beta glucan, DL panthenol, grape seed extract, magnesium ascorbyl phosphate and superoxide dismutase.
[5]This cell culture was exposed to UV light in the absence of added antioxidant materials.

The data for the assay of the production of PGE$_2$ are shown in Table 2. These results show that Blends A and B provide statistically significant protection from ultraviolet light when assayed for PGE$_2$. Production of PGE$_2$ resulting from ultraviolet light exposure for Blends A, B, and C is shown in Table 4. Blend B provides statistically superior protection from the production of PGE$_2$ when compared to its constituent ingredients. This statement is also valid for Blend A. Although not as effective as Blend A or Blend B, the PGE$_2$ produced is also noted to be as low with grape seed extract and magnesium ascorbyl phosphate alone.

TABLE 2

Production of PGE$_2$ Resulting from UV Light Exposure

| Antioxidant Agent Tested | Average PGE$_2$ Produced + Standard Deviation | Statistically Different from UV Irradiation Only (Confidence Level)[1] |
|---|---|---|
| Beta Glucan | 14,900 ± 3630 | No |
| DL Panthenol | 18,300 ± 5700 | No |
| Grape Seed Extract | 13,300 ± 2640 | No |
| Magnesium Ascorbyl Phosphate[2] | 15,100 ± 5390 | No |
| Superoxide Dismutase | 22,900 ± 19,500 | No |
| Vitamin A Palmitate | 17,400 ± 5720 | No |
| Vitamin E Acetate | 26,000 ± 2750 | No |
| Blend A[3] | 7140 ± 538 | Yes (85%) |
| Blend B[4] | 861 ± 135 | Yes (95%) |
| UV Irradiation Only[5] | 22,900 ± 11,000 | — |

[1]The level of statistical confidence is based upon hypothesis testing using a Student t test.
[2]This a stabilized form of Vitamin C (Ascorbic Acid).
[3]Blend A is composed of Vitamin A Palmitate and Vitamin E Acetate.
[4]Blend B is composed of Beta Glucan, DL Panthenol, Grape Seed Extract, Magnesium Ascorbyl Phosphate and Superoxide Dismutase.
[5]This cell culture was exposed to UV light in the absence of added antioxidant materials.

Although many of these ingredients have been used in skin care products previously, the combinations are unique. The use of beta glucan to interfere with the production of an inflammatory mediator (such as PGE$_2$), or to increase cellular viability following exposure to ultraviolet radiation, is also believed to be unique. Furthermore, the finding that these blends of antioxidant agents exhibit superior protection when mixed together is unexpected.

The combination of blends A and B, which is designated as Blend C in Table 3, was shown to provide statistically significant protection against the damaging effects of ultraviolet light using skin cell cultures. A comparison of this blend of antioxidants was found to be similar to the level of protection afforded by its oil and water soluble component blends. Based upon the results shown in Tables 1 and 2, there is evidence that Blend C provides more protection than its component ingredients. The data obtained from these tests are shown in Tables 3 through 6.

As shown in Examples 1 and 2, Blends A and B both provide statistically significant protection from the damaging effects of ultraviolet light in both the Percent Cellular Viability and PGE$_2$ production assays. As further shown in Tables 3 and 4, Blend C (which is composed of the ingredients in both Blends A and B) also showed statistically significant protection in these same tests when compared to cell cultures without the addition of the antioxidants.

Regarding the results obtained specifically from the Percent Cellular Viability assay method as shown in Table 5, Blend A was found to provide statistically better protection than Blend C. Blends A and B were not found to provide statistically different levels of protection by this method nor were Blends B and C found to provide statistically different levels of protection from the damaging effects of ultraviolet light. In the previous test procedure (see Table 1) the same relationship was found for Blends A and B.

The results obtained specifically from the $PGE_2$ Production assay method are shown in Table 6, which illustrates that Blend B was found to provide statistically better protection than Blend A. This is the same result found in the previous test (Table 2) where Blend B showed substantially greater reduction of $PGE_2$ production than Blend A. As shown in Tables 4 and 6, Blend C was found to provide statistically better protection than Blend A. However, Blend B was also found to provide statistically better protection than Blend C by this assay for $PGE_2$ production.

The fact that Blend A exhibits the best protection in the Percent Cellular Viability assay while Blend B exhibits the best protection in the $PGE_2$ Production assay may seem inconsistent. However, these two assays methods are different. The Reactive Oxygen Species (ROS) generated by ultraviolet light and that give rise to the damage detected by each assay method probably occurs from different biological pathways, thereby leading to different results. This explains why the water soluble antioxidants present in Blend B yield better protection in the $PGE_2$ production assay, whereas the oil soluble antioxidants present in Blend A yield better protection in the Percent Cellular Viability assay.

Blend A was also found to provide statistically better protection in the Percent Cellular Viability assay method as compared to Blend C, whereas Blend C was found to be statistically superior for the $PGE_2$ production assay. Similarly, although Blend B provides statistically better protection than Blend C in the $PGE_2$ Production assay, it is not statistically different from Blend C in the Percent Cellular Viability assay.

Although there are some statistical differences between the Blend C and blends of its oil or water soluble components, Blend C exhibits significant antioxidant activity in comparison to the individual ingredients tested previously.

Anyone skilled in the art of formulation will know how to readily incorporate these blends of antioxidant agents into suitable skin care and colored cosmetic products or into pharmaceutical products. Therefore, this information is intended to cover all possible combinations of these antioxidants in product formulations regardless of type or the market in which they are sold.

TABLE 3

Percent Cellular Viability Resulting from UV Light Exposure

| Antioxidant System | Average Percent Viability + Standard Deviation | Statistically Different from UV Irradiation Only (Confidence Level)[1] |
|---|---|---|
| Blend A[2] | 49.0 ± 4.1 | Yes (95%) |
| Blend B[3] | 42.0 ± 7.4 | Yes (95%) |
| Blend C[4] | 38.2 ± 1.7 | Yes (95%) |

[1]The level of statistical confidence is based upon hypothesis testing using a Student t test.
[2]Blend A is composed of Vitamin A palmitate and Vitamin E acetate.
[3]Blend B is composed of beta glucan, DL panthenol, grape seed extract, magnesium ascorbyl phosphate and superoxide dismutase.
[4]Blend C is a mixture of Blends A and B.

TABLE 4

Production of $PGE_2$ Resulting from UV Light Exposure

| Antioxidant System | Average $PGE_2$ Production + Standard Deviation | Statistically Different from UV Irradiation Only (Confidence Level)[1] |
|---|---|---|
| Blend A[2] | 4380 ± 545 | Yes (95%) |
| Blend B[3] | 2370 ± 352 | Yes (95%) |
| Blend C[4] | 2940 ± 123 | Yes (95%) |

[1]The level of statistical confidence is based upon hypothesis testing using a Student t test.
[2]Blend A is composed of Vitamin A palmitate and Vitamin E acetate.
[3]Blend B is composed of beta glucan, DL panthenol, grape seed extract, magnesium ascorbyl phosphate and superoxide dismutase.
[4]Blend C is a mixture of Blends A and B.

TABLE 5

Statistical Comparison of Percent Cellular Viability Resulting from UV Light Exposure

| Antioxidant System | Blend B[3] | Blend C[4] | UV Irradiation Only[5] |
|---|---|---|---|
| Blend A[2] | NSD[6] | 95% | 95% |
| Blend B[3] | — | NSD | 95% |
| Blend C[4] | — | — | 95% |

[1]The values listed in this table are the statistical confidence level of difference based upon hypothesis testing using a Student t test.
[2]Blend A is composed of Vitamin A Palmitate and Vitamin E acetate.
[3]Blend B is composed of beta glucan, DL panthenol, grape seed extract, magnesium ascorbyl phosphate and superoxide dismutase.
[4]Blend C is a mixture of Blends A and B
[5]This cell culture was exposed to UV light in the absence of added antioxidant materials.
[6]NSD is an abbreviation for Not Statistically Different.

TABLE 6

Statistical Comparison of $PGE_2$ Production Resulting from UV Light Exposure[1]

| Antioxidant System | Blend B[3] | Blend C[4] | UV Irradiation Only[5] |
|---|---|---|---|
| Blend A[2] | 95% | 95% | 95% |
| Blend B[3] | — | 90% | 95% |
| Blend C[4] | — | — | 95% |

[1]The values listed in this table are the statistical confidence level of difference based upon hypothesis testing using a Student t test.
[2]Blend A is composed of Vitamin A palmitate and Vitamin E acetate.
[3]Blend B is composed of beta glucan, DL panthenol, grape seed extract, magnesium ascorbyl phosphate and superoxide dismutase.
[4]Blend C is a mixture of Blends A and B.
[5]This cell culture was exposed to UV light in the absence of added antioxidant materials.

EXAMPLE 3

The following formulations demonstrate the typical use of the protective skin composition of the present invention in skin care and over the counter (OTC) pharmaceutical products. These formulations are listed only as examples of the types of compositions that could be used, and are not all encompassing of the possible uses of the technology in skin care and OTC pharmaceutical products. One skilled in the art of formulation will readily envision other possible uses for this technology, and the invention is not restricted the use of the formulations listed below. All ingredients of the formulations listed below are shown in percentage by weight (% w/w).

EXAMPLE 3

Liquid formulations
The following is a general formula for ligand formulations of the composition.

| Materials | General Use Range (Wt %) |
|---|---|
| Purified Water | 19.00000–98.71330 |
| Surfactants | 0.50–5.00 |
| Witch Hazel Distillate | 0.01–20.00 |
| Humectant | 0.50–5.00 |
| Fragrance | 0.01–1.00 |
| Preservatives | 0.20–3.00 |
| Sequestering Agent | 0.01–0.50 |
| Menthol | 0.005–1.00 |
| Vitamin A Palmitate | 0.0005–0.50 |
| Vitamin E Acetate | 0.05–30.00 |
| Magnesium Ascorbyl Phosphate | 0.0001–3.00 |
| Beta Glucan | 0.005–5.00 |
| Superoxide Dismutase | 0.0001–1.00 |
| Grape Seed Extract | 0.00001–1.00 |
| Panthenol | 0.005–5.00 |
| Total | 100.00000% |

EXAMPLE 4

Skin Toner
The following formulation was developed as a toner for the skin.

| Materials | Specific Use Concentration (Wt %) |
|---|---|
| Purified Water | 79.4719 |
| Surfactants | 2.0000 |
| Witch Hazel Distillate | 15.0000 |
| Humectant | 1.0000 |
| Fragrance | 0.0350 |
| Preservatives | 1.9000 |
| Sequestering Agent | 0.1000 |
| Menthol | 0.0100 |
| Plant Extracts | 0.0700 |
| Vitamin A Palmitate | 0.0050 |
| Vitamin E Acetate | 0.1000 |
| Magnesium Ascorbyl Phosphate | 0.0040 |
| Beta Glucan | 0.1000 |
| Superoxide Dismutase | 0.0040 |
| Grape Seed Extract | 0.0001 |
| Panthenol | 0.2000 |
| Total | 100.0000% |

EXAMPLE 5

Oil-in-Water (O/W) Emulsion
The following is a general formulation for an oil-in-water emulsion of a composition in accordance with the present invention.

| Materials | General Use Range (Wt %) |
|---|---|
| Purified Water | 0.0000–97.8173 |
| O/W Emulsifiers | 1.00–12.00 |
| Humectants | 0.50–15.00 |
| Fragrance | 0.001–1.00 |
| Preservatives | 0.10–3.00 |
| Sequestering Agent | 0.01–0.50 |
| Emollients | 0.50–30.00 |
| Thickeners | 0.01–1.00 |
| Vitamin A Palmitate | 0.0005–0.50 |
| Vitamin E Acetate | 0.05–30.00 |
| Magnesium Ascorbyl Phosphate | 0.0001–3.00 |
| Beta Glucan | 0.005–5.00 |
| Superoxide Dismutase | 0.0001–1.00 |
| Grape Seed Extract | 0.00001–1.00 |
| Panthenol | 0.005–5.00 |
| Total | 100.00000% |

EXAMPLE 6

Skin Moisturizing lotion
The following oil-in-water formulation was developed as a moisturizing lotion for the skin.

| Materials | Specific Use Concentration (Wt %) |
|---|---|
| Purified Water | 79.4719 |
| O/W Emulsifiers | 11.0000 |
| Humectants | 5.0000 |
| Fragrance | 0.0500 |
| Preservatives | 2.7000 |
| Sequestering Agent | 0.1000 |
| Emollients | 12.0000 |
| Thickeners | 0.3000 |
| Vitamin A Palmitate | 0.0500 |
| Vitamin E Acetate | 1.0000 |
| Magnesium Ascorbyl Phosphate | 0.2500 |
| Beta Glucan | 1.0000 |
| Superoxide Dismutase | 0.0400 |
| Grape Seed Extract | 0.0050 |
| Panthenol | 2.0000 |
| Total | 100.0000% |

EXAMPLE 7

Water-in-Oil (W/O) Emulsion
The following is a general formulation for a water-in-oil emulsion in accordance with the present invention.

| Materials | General Use Range (Wt %) |
|---|---|
| Purified Water | 0.0000–97.8173 |
| W/O Emulsifiers | 1.00–10.00 |
| Humectants | 0.00–10.00 |
| Fragrance | 0.00–0.50 |
| Preservatives | 0.10–7.00 |
| Sequestering Agent | 0.01–0.50 |
| Emollients and Sunscreen Agents | 10.00–60.00 |
| Salt | 0.01–1.00 |
| Vitamin A Palmitate | 0.0005–0.50 |
| Vitamin E Acetate | 0.05–30.00 |
| Magnesium Ascorbyl Phosphate | 0.0001–3.00 |
| Beta Glucan | 0.005–5.00 |
| Superoxide Dismutase | 0.0001–1.00 |
| Grape Seed Extract | 0.00001–1.00 |
| Panthenol | 0.005–5.00 |
| Total | 100.00000% |

EXAMPLE 8

Water-in-Oil Sunscreen Formulation
The following formulation was developed as a waterproof sunscreen product for the skin.

| Materials | Specific Use Concentration (Wt %) |
|---|---|
| Purified Water | 61.7865 |
| W/O Emulsifiers | 6.0000 |
| Preservatives | 3.6500 |
| Sequestering Agent | 0.1000 |
| Emollients and Sunscreens Agents | 27.7500 |
| Salt | 0.3000 |
| Vitamin A Palmitate | 0.0050 |
| Vitamin E Acetate | 0.1000 |
| Magnesium Ascorbyl Phosphate | 0.0040 |
| Beta Glucan | 0.1000 |
| Superoxide Dismutase | 0.0040 |
| Grape Seed Extract | 0.0005 |
| Panthenol | 0.2000 |
| Total | 100.0000% |

EXAMPLE 9

Synthetic (Moisturizing) Soap Bar
The following is a general formulation for a moisturizing soap bar.

| Materials | General Use Range (Wt %) |
|---|---|
| Purified Water | 0.00–15.00 |
| Detergents and Cleansing Agents | 32.0000–97.9573 |
| Buffering Agents | 1.00–3.00 |
| Humectants and Skin Conditioning Agents | 0.50–5.00 |
| Fragrance | 0.001–1.00 |
| Preservatives | 0.01–2.00 |
| Thickeners and Coloring Agents | 0.01–30.00 |
| Vitamin A Palmitate | 0.0005–0.50 |
| Vitamin E Acetate | 0.05–30.00 |
| Magnesium Ascorbyl Phosphate | 0.0001–3.00 |
| Beta Glucan | 0.005–5.00 |
| Superoxide Dismutase | 0.0001–1.00 |
| Grape Seed Extract | 0.00001–1.00 |
| Panthenol | 0.005–5.00 |
| Total | 100.00000% |

EXAMPLE 10

Moisturizing Soap Bar
The following formulation was developed as a moisturizing soap bar for sensitive facial skin.

| Materials | Specific Use Concentration (Wt %) |
|---|---|
| Purified Water | 9.3400 |
| Detergents and Cleansing Agents | 48.2000 |
| Buffering Agents | 2.4800 |
| Humectants and Skin Conditioning Agents | 13.0870 |
| Fragrance | 0.2400 |
| Preservatives | 0.0900 |
| Thickeners and Colorants | 25.6600 |
| Vitamin A Palmitate | 0.0050 |
| Vitamin E Acetate | 0.4900 |
| Magnesium Ascorbyl Phosphate | 0.0040 |
| Beta Glucan | 0.0100 |
| Superoxide Dismutase | 0.0040 |
| Grape Seed Extract | 0.1950 |
| Panthenol | 0.1910 |
| Total | 100.0000% |

Possible surfactants include polyoxyethylene sorbitan esters of fatty organic acids (such as laureate, palmitate, stearate, oleate and myristate) containing various molar concentrations of ethylene oxide (commonly listed as polysorbate 20, 21, 40, 60, 61, 65, 80, 81 and 85) as well as combinations of these ingredients.

Possible humectants include sugars (such as sorbitol, glucose, etc.), glycerin (and its polymers), glycols (such as propylene glycol, butylene glycol, and polyethylene glycols of various molecular weights); hyaluronic acid (and its salts), pyrrolidone carboxylic acid (and its salts) as well as combinations of these ingredients.

Possible preservatives include the parabens (such as the methyl, ethyl, propyl, isopropyl, butyl and isobutyl esters), imidazolidinyl urea, diazolidinyl urea, quaternium-15, phenylethyl alcohol, benzyl alcohol, phenoxyethanol, chlorphenesin, chlorhexidine digluconate as well as combinations of these ingredients.

Possible sequestering agents include the various salts of ethylenediamine tetraacetic acid (sodium, potassium, amine and amino acid salts).

Magnesium ascorbyl phosphate is a stabilized form of Vitamin C.

Stabilized forms of Vitamin A can be used in the preferred embodiment of the invention, such as the alcohol retinol or any of its esters. Other forms (such as Retin A) could also be used, but are less stable. Vitamin E is preferably used in its alcohol form (tocopherol), or any of its esters, or other stabilized forms.

Possible O/W surfactants include the salts of fatty acids (such as sodium, potassium, amine or amino acid salts of stearic, myristic, oleic, lauric or palmitic acid), non-ionic surfactants such as the polysorbates listed above, sorbitan esters of fatty acids (such as stearates, myristates, oleates, laureates, and palmitates), glyceryl esters of fatty acids (stearate, myristate, oleate, laureate and palmitate), polyoxyethylene esters of lanolin acids, alcohols and other wool wax components, polyoxyethylene ethers of fatty alcohols (such as lauryl, cetyl, oleyl and stearyl), polyethylene glycol esters of fatty acids (such as laureate, stearate, myristate, oleate, and palmitate), homo- and mixed block polymers of polyoxyethylene and polyoxypropylene, polyoxypropylene esters of fatty acids, polyoxypropylene ethers of fatty alcohols, sugar esters of fatty acids (such as the fatty acid esters of glucose and sucrose) and quaternary amine salts of fatty acids as well as combinations of these ingredients chosen to yield an oil-in-water emulsion.

Possible emollients include esters of fatty acids and fatty alcohols (such as octyl palmitate, octyl stearate, cetearyl stearate, etc.), silicone compounds (such as dimethicone, cyclomethicone, phenyltrimethicone, etc.), esters of organic acids and organic alcohols (C12–15 alkyl benzoate, octyl dodecanol, cetyl lactate, tridecyl trimellitate, octyldodecyl neopentanoate, etc.), fatty alcohols (cetyl alcohol, stearyl alcohol, etc.), castor oils, fractions of castor oils and their hydrogenated derivatives as well as combinations of these types of ingredients.

Possible thickeners include acrylic acid polymers and their cross polymer derivatives, polyvinylpyrrolidone polymers, natural polymers (such as locus bean gum, xanthan gum, alginic acid and its salts, dextran, etc.), clays (hectorite, montmorillonite, etc.) as well as combinations of these ingredients.

Possible water-in-oil (W/O) emulsifiers include the appropriate combinations of the oil-in-water emulsifiers listed above as well as cetyl dimethicone copolyols and other various other dimethicone copolyols in addition to combinations of these ingredients.

Possible emollients and sunscreens include the emollients listed above, as well as any approved sunscreen agents such as dioxybenzone, homomenthyl salicylate, menthyl anthranilate, octocrylene, octyl methoxycinnamate, octyl paraaminobenzoate, octyl salicylate, oxybenzone, and trolamine salicylate, as well as combinations of these ingredients.

Possible salts include sodium chloride, potassium chloride, lithium chloride and magnesium chloride or combinations of these ingredients.

Possible detergents and cleansing agents include the salts of cocyl isethionate, isostearoyl lactylate salts (such as the sodium and potassium salts), tallow and tallow salts (such as sodium, potassium and ammonium salts), salts of lauryl and laureth sulfates (such as sodium, potassium and ammonium salts), betaines and sultaines (such as cocamidopropyl betaine or sultaine) and salts of fatty acids (such as sodium or potassium laureate, myristate, palmitate, stearate, oleate, behenate, linoleate and ricinoleate) as well as combinations of these ingredients.

Possible buffering agents include all conventional buffering systems use in chemistry but especially lactic acid combined with a salt of lactic acid (such as sodium lactate) in appropriate ratios to maintain a given pH value.

Possible humectants and skin conditioning agents include the humectants listed above, salts of isostearoyl lactylate (such as sodium or potassium), quaternium compounds (such as stearamidopropyl dimethylamine) and oat by-products (such as oat flour) as well as combinations of these ingredients.

Possible thickeners and colorants include those thickeners listed above (see footnote 8) and colorants such as titanium dioxide, iron oxides, FD&C and D&C colorants, ultramarine blue, carmine, annatto, chlorophyll and other natural or artificial colorants as well as combinations of these ingredients.

The present invention takes advantage of the surprising superiority found when combining two skin agents that protect the skin from ultraviolet radiation, one agent from a class of protectants that increases cellular viability, and the other from a class that decreases the production of $PGE_2$ in the skin, as measured by the assays of Example 1. The compositions of the invention can be applied to skin both before or after exposure to ultraviolet radiation, to provide the protective effect, however application before exposure to the sun is preferred. Daily applications of the skin protectant may be used, even if exposure to the sun is not anticipated, to diminish the aging effects of ROS in the skin.

As used in this specification, reducing damage caused by exposure to ultraviolet radiation means reducing damage as measured by the assays of Example 1 (increased epidermal cellular viability) or Example 2 (reduced $PGE_2$ production by epidermal cells). Ultraviolet radiation refers to electromagnetic radiation having a wavelength shorter than the wavelengths of visible light and longer than those of x-rays. Skin injury refers to cellular damage as measured by decreased cellular viability or increased $PGE_2$ production, or both. An antioxidant is a substance that opposes the effects of ROS, either by scavenging or reducing ROS, or interfering with the production of ROS.

In view of the many possible embodiments to which the principles of my invention may be applied, it should be recognized that the illustrated embodiments are only specific examples of the invention and should not be taken as a limitation on the scope of the invention. Rather, the scope of the invention is defined by the following claims. I therefore claim as my invention all that comes within the scope and spirit of these claims.

What is claimed is:

1. A topical composition for reducing skin damage induced by ultraviolet radiation, the composition comprising:

beta glucan and grape seed extract in a sufficient amount to reduce the skin damage when the beta glucan and grape seed extract is applied topically; and at least one other skin protectant that reduces the skin damage caused by ultraviolet light.

2. The topical composition of claim 1, wherein the composition comprises panthenol, grape seed extract, beta glucan, Vitamin C and superoxide dismutase in a sufficient amount to reduce production of $PGE_2$, or increase cellular viability, in the skin when applied topically.

3. The composition of claim 2, wherein the composition further comprises an antioxidant selected from the group consisting of one or both of Vitamin A and Vitamin E in a sufficient amount to reduce reactive oxygen species in the skin when applied topically.

4. The topical composition of claim 2, wherein the composition comprises about: 0.005–5% beta glucan, 0.005–5% panthenol, 0.00001–1% grape seed extract, 0.0001–3% Vitamin C, and 0.0001–1% superoxide dismutase.

5. The topical composition of claim 2, wherein the composition comprises about: 0.0005–0.5000% Vitamin A and 0.0500–30% Vitamin E.

6. The topical composition of claim 2, wherein the composition further comprises at least about 0.0005% Vitamin A, and at least about 0.01% Vitamin E.

7. The topical composition of claim 4, wherein the Vitamin C is in the form of magnesium ascorbyl phosphate.

8. The topical composition of claim 5, wherein the Vitamin A is in the form of Vitamin A palmitate and the Vitamin E is in the form of Vitamin E acetate.

9. The topical composition of claim 2, wherein the other skin protectant is a protectant that improves cellular viability following exposure to ultraviolet radiation.

10. A topical composition for protecting skin against damage from ultraviolet radiation, comprising:

beta glucan, panthenol, grape seed extract, Vitamin C and superoxide dismutase in a sufficient amount to improve cellular viability and reduce the production of $PGE_2$ in the skin to which the composition is applied, after the skin is exposed to ultraviolet radiation.

11. The topical composition of claim 10, further comprising Vitamin A and Vitamin E in sufficient amounts to have an antioxidant effect on the skin when topically applied.

12. A composition for protecting skin against damage from ultraviolet radiation, comprising by weight at least about:

0.005% beta glucan;

0.005% panthenol;

0.00001% grape seed extract;

0.0001% Vitamin C; and 0.0001% superoxide dismutase.

13. The composition of claim 12, wherein the composition comprises by weight about:

0.005–5% beta glucan;

0.005–5% panthenol;

0.00001–1% grape seed extract;

0.0001–3% Vitamin C; and 0.0001–1% superoxide dismutase.

14. The composition of claim 12, further comprising by weight at least about 0.0005% Vitamin A, and at least 0.05% Vitamin E.

15. The composition of claim 13, further comprising by weight about:

0.0005–0.5000% Vitamin A; and 0.0100–30% Vitamin E.

16. The composition of claim 1, in an aqueous or non-aqueous solution, suspension, a water-in-oil or oil-in-water emulsion.

17. The composition of claim 1 in a skin toner composition, a moisturizing lotion, a sunscreen composition, a skin cleanser or other skin treatment composition.

18. A topical antioxidant composition comprising a sufficient amount of grape seed extract and beta glucan, wherein topical administration of said composition to epidermis increases cellular viability of epidermal cells, and decreases the production of $PGE_2$ in the epidermal cells, following exposure of the cells to ultraviolet radiation.

19. A composition comprising about:

(a)

|  | Percent by weight |
| --- | --- |
| Purified Water | 19.00000–98.71330 |
| Surfactants | 0.50–5 |
| Witch Hazel Distillate | 0.01–20 |
| Humectant | 0.50–5 |
| Fragrance | 0.001–1 |
| Preservatives | 0.20–3 |
| Sequestering Agent | 0.01–0.50 |
| Menthol | 0.005–1 |
| Vitamin A Palmitate | 0.0005–0.50 |
| Vitamin B Acetate | 0.05–30 |
| Magnesium Ascorbyl Phosphate | 0.0001–3 |
| Beta Glucan | 0.005–5 |
| Superoxide Dismutase | 0.0001–1 |
| Grape Seed Extract | 0.00001–1 |
| Panthenol | 0.005–5 |
| Total | 100.00000% | or (b)

|  | Percent by weight |
| --- | --- |
| Purified Water | 0.0000–97.8173 |
| O/W Emulsifiers | 1.00–12 |
| Humectants | 0.50–15 |
| Fragrance | 0.001–1 |
| Preservatives | 0.10–3 |
| Sequestering Agent | 0.01–0.50 |
| Emollients | 0.50–30 |
| Thickeners | 0.01–1 |
| Vitamin A Palmitate | 0.0005–0.50 |
| Vitamin E Acetate | 0.05–30 |
| Magnesium Ascorbyl Phosphate | 0.0001–3 |
| Beta Glucan | 0.005–5 |
| Superoxide Dismutase | 0.0001–1 |
| Grape Seed Extract | 0.001–1 |
| Panthenol | 0.005–5 |
| Total | 100.00000% | or (c)

|  | Percent by weight |
| --- | --- |
| Purified Water | 0.0000–97.8173 |
| W/O Emulsifiers | 1.00–10 |
| Humectants | 0.00–10 |
| Fragrance | 0.00–0.50 |
| Preservatives | 0.10–7 |
| Sequestering Agent | 0.01–0.50 |
| Emollients and Sunscreen Agents | 10.00–60 |
| Salt | 0.01–1 |
| Vitamin A Palmitate | 0.0005–0.50 |
| Vitamin E Acetate | 0.01–30 |
| Magnesium Ascorbyl Phosphate | 0.0001–3 |
| Beta Glucan | 0.005–5 |
| Superoxide Dismutase | 0.0001–1 |
| Grape Seed Extract | 0.001–1 |
| Panthenol | 0.005–5 |
| Total | 100.00000% | or (d)

|  | Percent by weight |
| --- | --- |
| Purified Water | 0.00–15 |
| Detergents and Cleansing Agents | 32.0000–97.9573 |
| Buffering Agents | 1.00–3 |
| Humectants and Skin Conditioning Agents | 0.50–5 |
| Fragrance | 0.001–1 |
| Preservatives | 0.01–2 |
| Thickeners and Coloring Agents | 0.01–30 |
| Vitamin A Palmitate | 0.0005–0.50 |
| Vitamin E Acetate | 0.01–30 |
| Magnesium Ascorbyl Phosphate | 0.0001–3 |
| Beta Glucan | 0.005–5 |
| Superoxide Dismutase | 0.0001–1 |
| Grape Seed Extract | 0.001–1 |
| Panthenol | 0.005–5 |
| Total | 100.00000% | or (e)

|  | Percent by Weight |
| --- | --- |
| Purified Water | 9.3400 |
| Detergents and Cleansing Agents | 48.2000 |
| Buffering Agents | 2.4800 |
| Humectants and Skin Conditioning Agents | 13.0870 |
| Fragrance | 0.2400 |
| Preservatives | 0.0900 |
| Thickeners and Colorants | 25.6600 |
| Vitamin A Palmitate | 0.0050 |
| Vitamin E Acetate | 0.4900 |
| Magnesium Ascorbyl Phosphate | 0.0040 |
| Beta Glucan | 0.0100 |
| Superoxide Dismutase | 0.0040 |
| Grape Seed Extract | 0.1950 |
| Panthenol | 0.1950 |
| Total | 100.0000% | or (f)

|  | Percent by weight |
| --- | --- |
| Purified Water | 79.4719 |
| O/W Emulsifiers | 11.0000 |
| Humectants | 5.0000 |
| Fragrance | 0.0500 |
| Preservatives | 2.7000 |
| Sequestering Agent | 0.1000 |
| Emollients | 12.0000 |
| Thickeners | 0.3000 |
| Vitamin A Palmitate | 0.0500 |
| Vitamin E Acetate | 1.0000 |
| Magnesium Ascorbyl Phosphate | 0.2500 |
| Beta Glucan | 1.0000 |
| Superoxide Dismutase | 0.0400 |
| Grape Seed Extract | 0.0050 |
| Panthenol | 2.0000 |
| Total | 100.0000% | or (g)

|  | Percent by weight |
| --- | --- |
| Purified Water | 79.4719 |
| Surfactants | 2.0000 |
| Witch Hazel Distillate | 15.0000 |
| Humectant | 1.0000 |
| Fragrance | 0.0350 |
| Preservatives | 1.9000 |
| Sequestering Agent | 0.1000 |
| Menthol | 0.0100 |
| Plant Extracts | 0.0700 |

-continued

|  | Percent by weight |
| --- | --- |
| Vitamin A Palmitate | 0.0050 |
| Vitamin E Acetate | 0.1000 |
| Magnesium Ascorbyl Phosphate | 0.0040 |
| Beta Glucan | 0.1000 |
| Superoxide Dismutase | 0.0040 |
| Grape Seed Extract | 0.0001 |
| Panthenol | 0.2000 |
| Total | 100.0000% |

20. A sunscreen product for the skin, comprising about:

|  | Percent by weight |
| --- | --- |
| Purified Water | 61.7865 |
| W/O Emulsifiers | 6.0000 |
| Preservatives | 3.6500 |
| Sequestering Agent | 0.1000 |
| Emollients and Sunscreens Agents | 27.7500 |
| Salt | 0.3000 |
| Vitamin A Palmitate | 0.0050 |
| Vitamin E Acetate | 0.1000 |
| Magnesium Ascorbyl Phosphate | 0.0040 |
| Beta Glucan | 0.1000 |
| Superoxide Dismutase | 0.0040 |
| Grape Seed Extract | 0.0005 |
| Panthenol | 0.2000 |
| Total | 100.0000% |

* * * * *